(12) United States Patent
Shi et al.

(10) Patent No.: US 11,398,644 B2
(45) Date of Patent: Jul. 26, 2022

(54) NON-AQUEOUS ELECTROLYTE FOR LITHIUM ION BATTERY AND LITHIUM ION BATTERY

(71) Applicant: SHENZHEN CAPCHEM TECHNOLOGY CO., LTD., Guangdong (CN)

(72) Inventors: Qiao Shi, Guangdong (CN); Shiguang Hu, Guangdong (CN); Zhaohui Deng, Guangdong (CN); Hao Zhang, Guangdong (CN); Chunhua Liu, Guangdong (CN)

(73) Assignee: SHENZHEN CAPCHEM TECHNOLOGY CO., LTD., Shenzhen (CN)

( * ) Notice: Subject to any disclaimer, the term of this patent is extended or adjusted under 35 U.S.C. 154(b) by 311 days.

(21) Appl. No.: 16/631,829

(22) PCT Filed: Dec. 28, 2017

(86) PCT No.: PCT/CN2017/119377
§ 371 (c)(1),
(2) Date: Jan. 16, 2020

(87) PCT Pub. No.: WO2019/024412
PCT Pub. Date: Feb. 7, 2019

(65) Prior Publication Data
US 2020/0144669 A1    May 7, 2020

(30) Foreign Application Priority Data
Jul. 31, 2017  (CN) .......................... 201710640474.6

(51) Int. Cl.
| | |
|---|---|
| *H01M 10/0567* | (2010.01) |
| *C07D 317/34* | (2006.01) |
| *C07D 327/00* | (2006.01) |
| *C07F 7/18* | (2006.01) |
| *H01M 4/505* | (2010.01) |
| *H01M 4/525* | (2010.01) |
| *H01M 4/58* | (2010.01) |
| *H01M 10/0525* | (2010.01) |
| *H01M 4/02* | (2006.01) |

(52) U.S. Cl.
CPC ...... *H01M 10/0567* (2013.01); *C07D 317/34* (2013.01); *C07D 327/00* (2013.01); *C07F 7/1804* (2013.01); *H01M 4/505* (2013.01); *H01M 4/525* (2013.01); *H01M 4/5825* (2013.01); *H01M 10/0525* (2013.01); *H01M 2004/028* (2013.01); *H01M 2300/0025* (2013.01)

(58) Field of Classification Search
CPC ..................... H01M 10/0567; H01M 10/0569
See application file for complete search history.

(56) References Cited

U.S. PATENT DOCUMENTS

| | | | |
|---|---|---|---|
| 3,663,569 A | 5/1972 | Lew | |
| 6,174,629 B1 | 1/2001 | Gan et al. | |
| 10,177,413 B2* | 1/2019 | Sasaki | H01M 10/0525 |
| 11,005,126 B2* | 5/2021 | Hiasa | H01M 10/0525 |
| 2011/0159382 A1* | 6/2011 | Matsui | H01M 10/0569 |
| | | | 429/338 |
| 2018/0102570 A1* | 4/2018 | Koh | H01M 10/0568 |

FOREIGN PATENT DOCUMENTS

| | | |
|---|---|---|
| CN | 1495959 A | 5/2004 |
| CN | 102195076 A | 9/2011 |
| CN | 103151559 A | 6/2013 |
| CN | 103354962 A | 10/2013 |
| CN | 103441304 A | 12/2013 |

(Continued)

OTHER PUBLICATIONS

Translation of JP 2006-219406 (no date).*

(Continued)

*Primary Examiner* — Amanda C. Walke

(57) ABSTRACT

Provided is a non-aqueous electrolyte for lithium ion battery, comprising a compound A represented by structural formula I and a compound B represented by structural formula II:

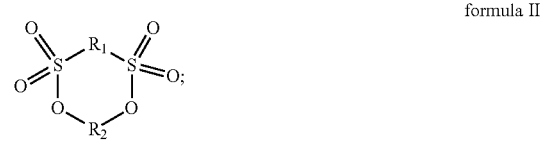

formula II

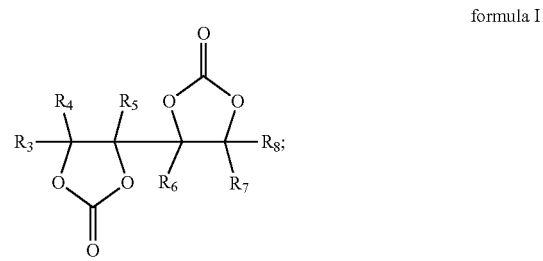

formula I

Wherein, in formula I, $R_1$ is selected from alkylene having 1-5 carbon atoms or fluorine substituted alkylene having 1-5 carbon atoms; $R_2$ is selected from anyone of alkylene having 1-5 carbon atoms, fluorine substituted alkylene having 1-5 carbon atoms or carbonyl; In formula II, $R_3$, $R_4$, $R_5$, $R_6$, $R_7$ and $R_8$ are each independently selected from hydrogen, fluorine atom or a group containing 1-5 carbon atoms. The compound A and compound B of the non-aqueous electrolyte can form a passivation film formed by reduction, decomposition and combination reactions on the surface of negative electrode material of lithium-ion battery, thereby improving thermal stability of the passivation film and high-temperature cycle and storage performance of the battery.

9 Claims, No Drawings

(56) References Cited

FOREIGN PATENT DOCUMENTS

| | | |
|---|---|---|
| CN | 103460496 A | 12/2013 |
| CN | 103594729 A | 2/2014 |
| CN | 104300174 A | 1/2015 |
| CN | 105051965 A | 11/2015 |
| CN | 105161763 A | 12/2015 |
| CN | 105580189 A | 5/2016 |
| CN | 105633461 A | 6/2016 |
| CN | 105830270 A | 8/2016 |
| CN | 106058317 A | 10/2016 |
| CN | 106252639 A | 12/2016 |
| CN | 106328996 A | 1/2017 |
| CN | 106410272 A | 2/2017 |
| GB | 1147540 A | 4/1969 |
| JP | 2000260467 A | 9/2000 |
| JP | 2006219406 A | 8/2006 |
| JP | 2014182951 A | 9/2014 |
| JP | 2014525667 A | 9/2014 |
| JP | 2015092476 A | 5/2015 |
| WO | 2016025589 A1 | 2/2016 |
| WO | 2016151983 A1 | 9/2016 |

OTHER PUBLICATIONS

International Search Report of PCT Patent Application No. PCT/CN2017/119377 dated Apr. 20, 2018.

Libo Hu et al., Fluorinated electrolytes for 5-V Li-ion chemistry: Dramatic enhancement of LiNi0.5Mn1.5O4/graphite cell performance by a lithium reservoir, Electrochemistry Communications, Apr. 2014, vol. 44, pp. 34-37.

* cited by examiner

NON-AQUEOUS ELECTROLYTE FOR LITHIUM ION BATTERY AND LITHIUM ION BATTERY

TECHNICAL FIELD

The application belongs to the technical field of lithium ion battery electrolyte, in particular to a non-aqueous electrolyte for lithium ion battery and a lithium ion battery.

BACKGROUND

Lithium ion battery has made great progress in the field of portable electronic products due to its high working voltage, high safety, long service life and no memory effect. Moreover, with the development of new energy vehicles, lithium ion batteries have shown great application prospects in power supply systems for new energy vehicles.

In non-aqueous electrolyte for lithium ion battery, non-aqueous electrolyte is the key factor affecting the high and low temperature performances of battery.

In particular, additives in non-aqueous electrolyte are particularly important for the performances of battery at high and low temperatures. Because in the initial charging process of lithium ion battery, lithium ions in the positive electrode material of the battery are released and embedded into the carbon negative electrode through electrolyte. Due to its high reactivity, electrolyte reacts on the surface of the carbon negative electrode to produce compounds such as Li2CO3, Li2O, LiOH, and etc, thus forming a passivation film on the surface of the negative electrode, which is called a solid electrolyte interface film (SEI). The SEI film formed during the initial charging process not only prevents the electrolyte from further decomposing on the surface of the carbon negative electrode, but also acts as a lithium ion channel, allowing only lithium ions to pass through. Therefore, SEI film determines the performance of lithium ion battery.

In order to improve the various performances of lithium ion batteries, many researchers have tried to improve the quality of SEI films by adding different negative film-forming additives (such as vinylene carbonate, fluoroethylene carbonate, vinylethylene carbonate) to the electrolyte.

Chinese patent application No. 03132755.9 discloses an electrolyte containing cyclic sulfonate ester with at least two sulfonyl groups for secondary battery, the cyclic sulfonate ester are helpful to form a passivation layer on the electrode interface of the battery and prevent decomposition of solvent molecules, thereby improving the cycle performance of the battery and inhibiting gas generation of the battery. Although the non-aqueous electrolyte containing cyclic sulfonate ester with two sulfonyl groups (such as methylene methanedisulfonate) can improve the normal temperature cycle performance of lithium ion battery and reduce the high-temperature storage gas generation of the battery to a certain extent, the high-temperature cycle performance of the battery is obviously insufficient, and the high-temperature storage performance of the batteries is still insufficient.

SUMMARY

The application aims to provide a non-aqueous electrolyte for lithium ion battery, in order to solve the problems of poor high-temperature cycle performance and poor storage performance of the existing lithium ion battery electrolyte.

Another object of the present application is to provide a lithium ion battery containing the above-mentioned non-aqueous electrolyte for lithium ion battery.

In order to achieve the above objects, the application adopts the following technical solution:

The application relates to a non-aqueous electrolyte for lithium ion battery, comprising a compound A represented by structural formula I and a compound B represented by structural formula II.

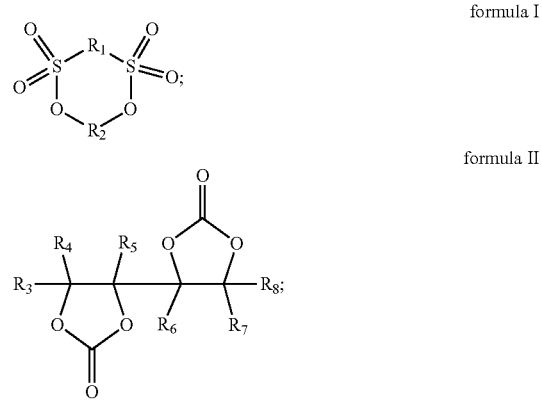

Wherein, in formula I, $R_1$ is selected from alkylene having 1-5 carbon atoms or fluorine substituted alkylene having 1-5 carbon atoms; $R_2$ is selected from any one of alkylene having 1-5 carbon atoms, fluorine substituted alkylene having 1-5 carbon atoms or carbonyl;

In formula II, $R_3$, $R_4$, $R_5$, $R_6$, $R_7$ and $R_8$ are each independently selected from hydrogen, fluorine atom or a group containing 1-5 carbon atoms.

Preferably, in the compound B represented by structural formula II, the group containing 1-5 carbon atoms is selected from hydrocarbyl, fluorinated hydrocarbyl, oxygen-containing hydrocarbyl, silicon-containing hydrocarbyl, or cyano-substituted hydrocarbyl.

Preferably, $R_3$, $R_4$, $R_5$, $R_6$, $R_7$ and $R_8$ are each independently selected from hydrogen atom, fluorine atom, methyl group, ethyl group, methoxy group, ethoxy group, trimethylsiloxy group, cyano group, or trifluoromethyl group.

Preferably, the compound A represented by structural formula I is selected from

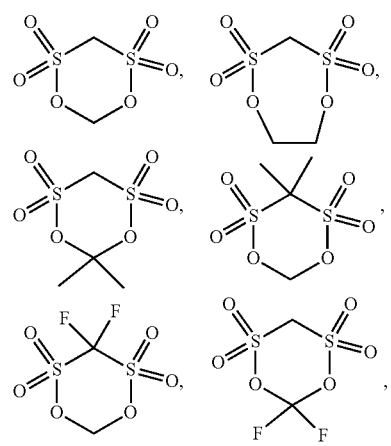

-continued

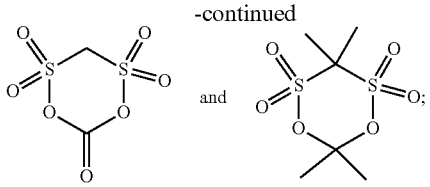

the compound B represented by structural formula II is at least one selected from

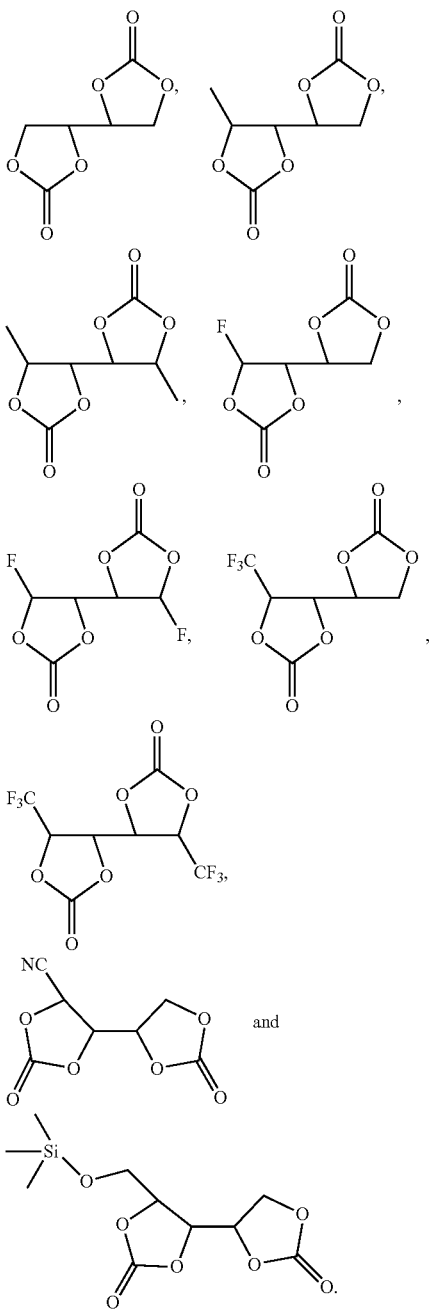

Preferably, the percentage mass content of the compound A is 0.1% to 2.0% based on the total mass of the non-aqueous electrolyte for lithium ion battery being 100%.

Preferably, the percentage mass content of the compound B is 0.1% to 5.0% based on the total mass of the non-aqueous electrolyte for lithium ion battery being 100%.

Preferably, the non-aqueous electrolyte further comprises at least one of unsaturated cyclic carbonate, fluorinated cyclic carbonate, and cyclic sultones.

Preferably, the unsaturated cyclic carbonate further comprises at least one of vinylene carbonate, vinylethylene carbonate, and methylene vinyl carbonate;
the fluorinated cyclic carbonate comprises at least one of fluoroethylene carbonate, trifluoromethyl vinyl carbonate and difluoroethylene carbonate;
the cyclic sultones comprises at least one of 1,3-propane sultone, 1,4-butane sultone and propenyl-1,3-sultone.

And a lithium ion battery, a separator for separating the positive electrode and the negative electrode, and an electrolyte, wherein the electrolyte is the above-mentioned non-aqueous electrolyte for lithium ion battery.

Preferably, the positive electrode comprises a positive electrode active material selected from at least one of $LiNi_xCo_yMn_zL_{(1-x-y-z)}O_2$, $LiCo_xL_{(1-x')}O_2$, $LiNi_{x'}L'_{y'}Mn_{(2-x''-y')}O_4$ and $Li_zMPO_4$; wherein L is at least one of Al, Sr, Mg, Ti, Ca, Zr, Zn, Si or Fe; $0≤x≤1$, $0≤y≤1$, $0≤z≤1$, $0<x+y+z≤1$, $0<x'≤1$, $0.3≤x''≤0.6$, $0.01≤y'≤0.2$; L' is at least one of Co, Al, Sr, Mg, Ti, Ca, Zr, Zn, Si, Fe; $0.5≤z'≤1$, M is at least one of Fe, Mn and co.

The lithium ion battery non-aqueous electrolyte provided by the invention comprises a compound A represented by structural formula I and a compound B represented by structural formula II. In the lithium ion battery, the compound A can decompose on the surface of the negative electrode prior to solvent molecules to form a passivation film during the first charging process of the battery, thereby inhibiting further decomposition of the electrolyte. However, the inventors of the present invention have found that the thermal stability of the passivation film is poor, and the passivation layer is likely to be damaged in the high-temperature cycle process of the battery, thus causing the battery performance to decline and the high-temperature cycle performance to be poor. The compound B can also undergo decomposition reaction on the surface of the negative electrode material to form a passivation film, and the thermal stability of the passivation film is high; when the compound B and the compound A are used together, a passivation film formed by reducing, decomposing and combining the compound A and the compound B is formed on the surface of the negative electrode material, so that the thermal stability of the passivation film is improved, the high-temperature cycle of the battery is improved, and the high-temperature storage performance is also improved.

The lithium ion battery provided by the application contains the non-aqueous electrolyte as its electrolyte, thus having better high-temperature cycle performance and high-temperature storage performance.

DETAILED DESCRIPTION OF DISCLOSED EMBODIMENT

In order to make the to-be-solved technical problems, technical solutions and beneficial effects of the present invention clearer, the present invention will be described in further detail below with reference to embodiments. It should be understood that the specific embodiments described herein are only for the purpose of explaining the present application and are not intended to limit the present application.

The embodiment of the application provides a non-aqueous electrolyte for lithium ion battery, which comprises a compound A represented by structural formula I and a compound B represented by structural formula II.

formula I

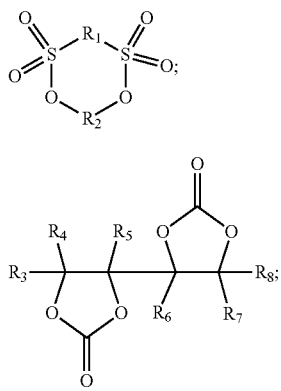

formula II

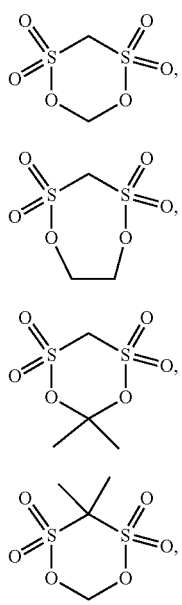

Wherein, in formula I, $R_1$ is selected from alkylene having 1-5 carbon atoms or fluorine substituted alkylene having 1-5 carbon atoms; $R_2$ is selected from any one of alkylene having 1-5 carbon atoms, fluorine substituted alkylene having 1-5 carbon atoms or carbonyl;

In formula II, $R_3$, $R_4$, $R_5$, $R_6$, $R_7$ and $R_8$ are each independently selected from hydrogen, fluorine atom or a group containing 1-5 carbon atoms.

Preferably, in the above structural formula II, the group containing 1-5 carbon atoms is selected from hydrocarbyl, fluorinated hydrocarbyl, oxygen-containing hydrocarbyl, silicon-containing hydrocarbyl, or cyano-substituted hydrocarbyl.

Preferably, $R_3$, $R_4$, $R_5$, $R_6$, $R_7$ and $R_8$ are each independently selected from hydrogen atom, fluorine atom, methyl group, ethyl group, methoxy group, ethoxy group, trimethylsiloxy group, cyano group, or trifluoromethyl group.

Preferably, the compound A represented by structural formula I is at least one of (A1)

(A2)

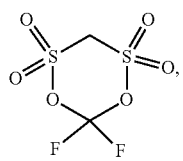

(A3)

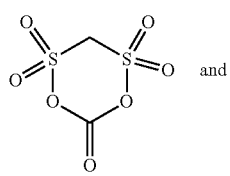

(A4)

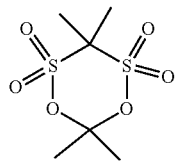

(A5)

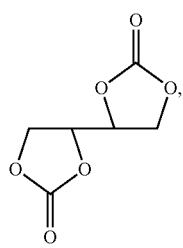

(A6)

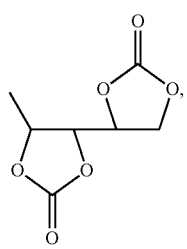

(A7) and

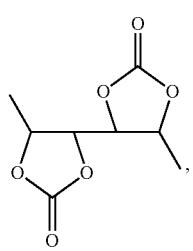

(A8)

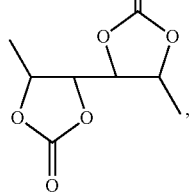

(for convenience of recording, A1 to A8 refer to corresponding compounds in this document).

Preferably, the compound B represented by structural formula II is at least one of 拆

(B1)

(B2)

(B3)

(B4) 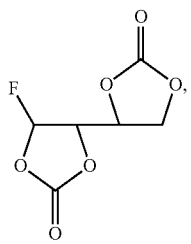

(B5) 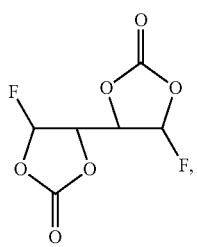

(B6) 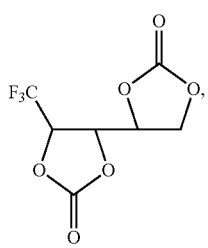

(B7) 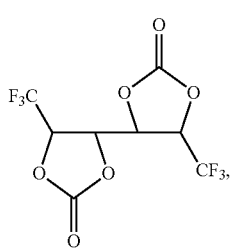

(B8) 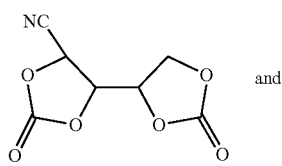

(B9) 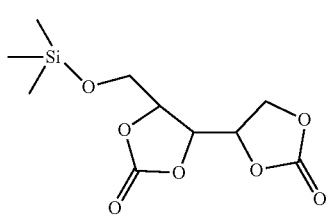

(for convenience of recording, B1 to B9 refer to corresponding compounds in this document).

The compound B represented by the above formula II can be prepared by transesterification of polyhydric alcohol (such as erythritol, xylitol, etc.) and carbonate (such as dimethyl carbonate, diethyl carbonate, ethylene carbonate, etc.) under the action of alkaline catalyst, and then recrystallization or column chromatography purification. The specific synthetic route is as follows:

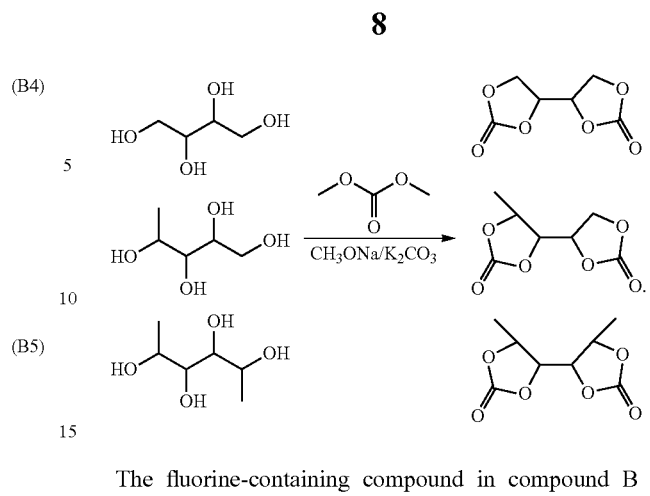

The fluorine-containing compound in compound B is prepared by fluorinating the mixture of the corresponding carbonate and $F_2/N_2$, and then recrystallizing or purifying by column chromatography. An example of its synthetic route is as follows:

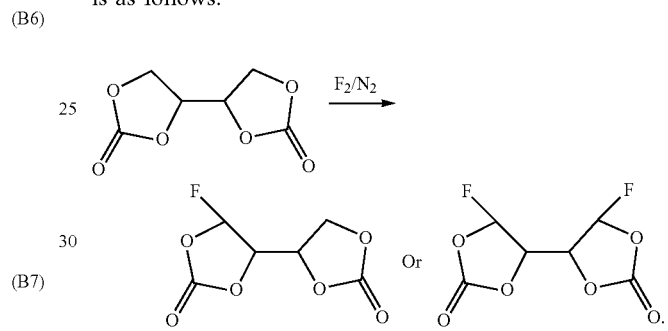

The cyano group-containing compound in compound B is prepared by chlorinating the corresponding carbonate with sulfonyl chloride, then reacting with NaCN or KCN, and purifying by recrystallization or column chromatography. An example of its synthetic route is as follows:

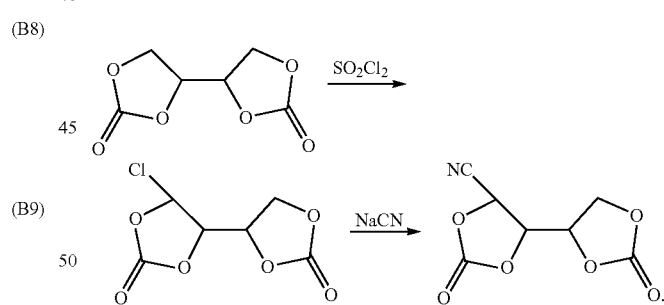

The trimethylsiloxy-containing compound in the compound B is prepared by carrying out substitution reaction on the corresponding hydroxy carbonate and the nitrogen silane, and then recrystallizing or purifying by column chromatography. An example of its synthetic route is as follows:

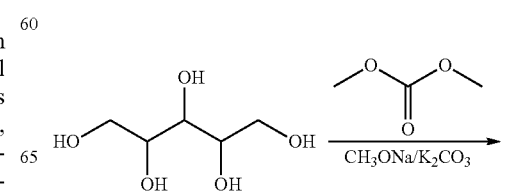

-continued

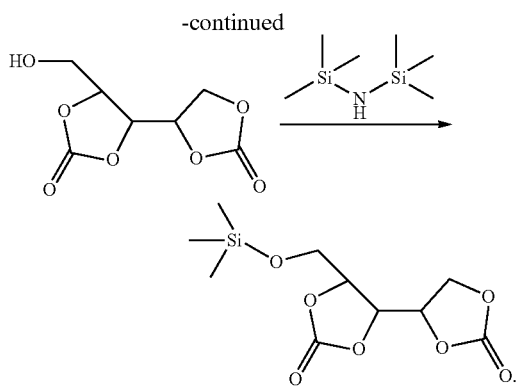

Preferably, the percentage mass content of the compound A is 0.1% to 2.0% based on the total mass of the non-aqueous electrolyte for lithium ion battery being 100%.

Preferably, the percentage mass content of the compound B is 0.1% to 5.0% based on the total mass of the non-aqueous electrolyte for lithium ion battery being 100%.

For example, the percentage mass content of the compound B may be 0.1%, 0.2%, 0.4%, 0.5%, 0.6%, 0.8%, 1%, 1.2%, 1.5%, 1.8%, 2%, 2.5%, 3%, 3.5%, 4%, 4.5%, 5%.

The non-aqueous electrolyte provided by the technical solution of the application comprises not only the above two material components, but also at least one of unsaturated cyclic carbonate, fluorinated cyclic carbonate, and cyclic sultones.

Preferably, the unsaturated cyclic carbonate is selected from at least one of vinylene carbonate (VC), vinylethylene carbonate (VEC), and methylene vinyl carbonate. The fluorinated cyclic carbonate is selected from at least one of fluoroethylene carbonate (FEC), trifluoromethyl vinyl carbonate and difluoroethylene carbonate. The cyclic sultones is selected from at least one of 1,3-propane sultone (1,3-PS), 1,4-butane sultone (1,4-BS) and propenyl-1,3-sultone.

As in the prior art, the non-aqueous electrolyte of the lithium ion battery contains a solvent and a lithium salt, and there is no specific limitation on the type and percentage content of the solvent in the solution of the application, for example, the solvent of the non-aqueous electrolyte for lithium ion battery comprises cyclic carbonate and chain carbonate.

Preferably, the cyclic carbonate comprises at least one of ethylene carbonate, propylene carbonate and butylene carbonate. The chain carbonate comprises at least one of dimethyl carbonate, diethyl carbonate, methyl ethyl carbonate and methyl propyl carbonate.

The lithium salt is not particularly limited in the present invention, and various existing lithium salts can be used, for example, the lithium salt can be selected from one or more of $LiPF_6$, LiFSI and $LiBF_4$. The content of the lithium salt can vary within a large range, and preferably, the percentage content of the lithium salt in the non-aqueous electrolyte for lithium ion battery is 0.1-15%.

When the non-aqueous electrolyte of the present application is used as the electrolyte for lithium ion battery, the compound A represented by structural formula I can decompose on the surface of the negative electrode prior to solvent molecules to form a passivation film during the first charging process of the battery, thereby inhibiting further decomposition of the electrolyte. However, the thermal stability of the passivation film is poor, and the passivation layer is likely to be damaged in the high-temperature cycle process of the battery. The compound B represented by structural formula II can also undergo decomposition reaction on the surface of the negative electrode material to form a passivation film, and the thermal stability of the passivation film is high. When the compound A represented by structural formula I and the compound B represented by structural formula II are used together, a passivation film formed by reduction, decomposition and combination reactions on the surface of the negative electrode material, thereby improving the thermal stability of the passivation film and improving the high-temperature cycle of the battery, and further improving the high-temperature storage performance.

On the premise of the lithium ion non-aqueous electrolyte, the embodiment of the application also provides a lithium ion battery.

In one embodiment, the lithium ion battery comprises a positive electrode, a negative electrode, a separator for separating the positive electrode and the negative electrode, and an electrolyte, wherein the electrolyte is the non-aqueous electrolyte for lithium ion battery.

Specifically, the positive electrode comprises a positive electrode active material, wherein the active material of the positive electrode is at least one of $LiNi_xCo_yMn_zL_{(1-x-y-z)}O_2$, $LiCo_xL_{(1-x)}O_2$, $LiNi_{x'}L'_{y'}Mn_{(2-x''-y')}O_4$ and $Li_zMPO_4$; wherein L is at least one of Al, Sr, Mg, Ti, Ca, Zr, Zn, Si or Fe; $0 \leq x \leq 1$, $0 \leq y \leq 1$, $0 \leq z \leq 1$, $0 < x+y+z \leq 1$, $0 < x' \leq 1$, $0.3 \leq x'' \leq 0.6$, $0.01 \leq y' \leq 0.2$; L' is at least one of Co, Al, Sr, Mg, Ti, Ca, Zr, Zn, Si, Fe; $0.5 \leq z' \leq 1$, M is at least one of Fe, Mn and co.

The active material of the negative electrode is selected from artificial graphite and natural graphite. Obviously, it is not limited to the two listed.

The separator is a conventional diaphragm in the field of lithium ion batteries, so it will not be limited in the present application.

The lithium ion battery provided by the embodiment of the application contains the non-aqueous electrolyte, thus has better high-temperature cycle performance and high-temperature storage performance.

In order to better illustrate the technical solution of the present application, the following description will be made with reference to specific embodiments.

It should be noted that in order to control a single variable, all embodiments of the present application use 4.2V $LiNi_{0.5}Co_{0.2}Mn_{0.3}O_2$/artificial graphite batteries as experimental batteries. Obviously, it should be noted that the non-aqueous electrolyte of the present invention is not only suitable for 4.2V $LiNi_{0.5}Co_{0.2}Mn_{0.3}O_2$/artificial graphite batteries.

Embodiment 1

A 4.2V $LiNi_{0.5}Co_{0.2}Mn_{0.3}O_2$/artificial graphite battery, comprising a positive electrode, a negative electrode, a separator arranged between the positive electrode and the negative electrode, an electrolyte and a battery case, wherein the electrolyte is a non-aqueous electrolyte and comprises a compound A and a compound B, and the compound A and the compound B comprise the following components in percentage by mass based on the total mass of the non-aqueous electrolyte being 100%.

Embodiments 2-14

To save space, Embodiments 2-14 are listed in Table 1.

Comparative Examples 1-5

Comparative Examples 1-5 are the same as Embodiment 1 except that the addictive components are different as shown in Table 1.

The lithium ion batteries prepared in Embodiments 1-14 and Comparative Examples 1-5 are subjected to corresponding performance tests, and the specific tests include a high-temperature cycle performance test and a high-temperature storage performance test.

The test method is as follows:

1. High-Temperature Cycle Performance Test

The lithium ion batteries prepared in Embodiments 1-14 and Comparative Examples 1-5 were placed in an oven at a constant temperature of 45° C., charged to 4.2V with 1C constant current, and charged till current drops to 0.02C with a constant voltage, then discharged to 3.0V with 1C constant current. The 1st discharge capacity and the last discharge capacity were recorded in this cycle.

The calculation formula of high-temperature cycle capacity retention rate is as follows: Capacity retention rate=last discharge capacity/1st discharge capacity×100%

2. High-Temperature Storage Performance Test

The formed lithium ion battery was charged to 4.2V at normal temperature with 1C constant current/constant voltage, and the initial discharge capacity and initial battery thickness of the battery were measured. Then the battery was stored at 60° C. for 30 days and discharged to 3V with 1C, the capacity retention, capacity recovery and battery thickness after stored were measured.

The calculation formula is as follows:

Battery capacity retention rate(%)=(retention capacity/initial capacity)×100%;

Battery capacity recovery rate(%)=(recovery capacity/initial capacity)×100%;

Battery thickness expansion rate(%)=(battery thickness after storage−initial battery thickness)/initial battery thickness×100%.

From the data in Table 1, it can be seen that, comparing Embodiments 1-10 and Comparative Example 1, when compound A represented by structural formula I is added alone, the high-temperature cycle and high-temperature storage performance of the battery are poor and need to be further improved. When the compound represented by structural formula I and the compound represented by structural formula II are both used, because of the formation of a passivation film with better thermal stability on the negative electrode, the high-temperature cycle and high-temperature storage performance of the battery can be obviously improved.

Meanwhile, it can be seen that the high-temperature cycle and storage performances of the battery can be further improved with the increase of the content of the compound B represented by structural formula II.

By comparing Embodiments 11-14 and comparative examples 2-5, it can be seen that the addition of the compound B on the basis of the compound A and VC, FEC, PS, Lithium difluorosulfonylimide (LiFSI) can further improve the high-temperature cycle and high-temperature storage of the battery.

The above descriptions are only preferred embodiments and are not intended to limit the present invention. Any modifications, equivalent substitutions and improvements made within the spirit and principles of the present invention shall be included within the scope of protection of the present invention. Further, unless otherwise required by context, singular terms shall include pluralities and plural terms shall include the singular. Thus, as used herein and in the claims, the singular forms include the plural reference and vice versa unless the context clearly indicates otherwise.

The invention claimed is:

1. A non-aqueous electrolyte for lithium ion battery, comprising a compound A represented by structural formula I and a compound B represented by structural formula II:

TABLE 1

Data of Embodiments 1-14 and Comparative Examples 1-5

| Embodiment | Compound represented by structural formula I and content thereof | Compound represented by structural formula II and content thereof | Other additives and contents | The 500th cycle capacity retention rate at 45° C. 1C | After 30 days of storage at 60° C. Retention rate/% | Recovery rate/% | Expansion rate/% |
|---|---|---|---|---|---|---|---|
| Embodiment 1 | A1:1% | B1:1% | / | 82.1 | 83.3 | 88.4 | 11.5 |
| Embodiment 2 | A3:1% | B2:1% | / | 82.5 | 84.1 | 89.0 | 10.4 |
| Embodiment 3 | A5:1% | B5:1% | / | 83.4 | 84.8 | 90.3 | 10.1 |
| Embodiment 4 | A7:1% | B8:1% | / | 83.8 | 85.2 | 91.4 | 9.2 |
| Embodiment 5 | A1:1% | B2:1% | / | 82.5 | 84.4 | 88.9 | 10.5 |
| Embodiment 6 | A1:0.5% | B1:0.5% | / | 80.2 | 81.4 | 86.5 | 13.5 |
| Embodiment 7 | A1:1% | B1:2% | / | 85.8 | 86.4 | 92.4 | 7.1 |
| Embodiment 8 | A1:1% | B1:3% | / | 86.9 | 87.8 | 93.4 | 5.4 |
| Embodiment 9 | A1:2% | B1:1% | / | 82.3 | 83.7 | 89.1 | 11.1 |
| Embodiment 10 | A1:2% | B1:2% | / | 86.1 | 86.5 | 92.6 | 7.0 |
| Embodiment 11 | A1:1% | B1:1% | VC:1% | 85.4 | 85.8 | 90.5 | 13.5 |
| Embodiment 12 | A1:1% | B1:1% | FEC:1% | 84.2 | 84.4 | 88.7 | 15.6 |
| Embodiment 13 | A1:1% | B1:1% | PS:1% | 82.4 | 86.5 | 92.1 | 10.4 |
| Embodiment 14 | A1:1% | B1:1% | LiFSI:1% | 83.7 | 85.3 | 90.5 | 11.3 |
| Comparative Example 1 | A1:1% | / | / | 65.4 | 75.4 | 80.8 | 15.4 |
| Comparative Example 2 | A1:1% | / | VC:1% | 81.3 | 82.4 | 87.4 | 17.8 |
| Comparative Example 3 | A1:1% | / | FEC:1% | 80.5 | 81.5 | 85.9 | 20.8 |
| Comparative Example 4 | A1:1% | / | PS:1% | 78.9 | 83.4 | 89.2 | 13.4 |
| Comparative Example 5 | A1:1% | / | LiFSI:1% | 79.6 | 82.4 | 87.6 | 14.2 | formula I

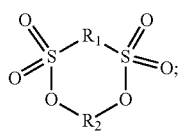

formula II

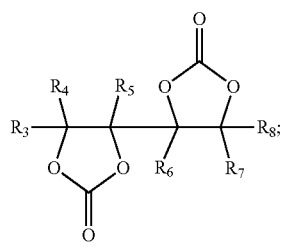

wherein, in formula I, is selected from alkylene having 1-5 carbon atoms or fluorine substituted alkylene having 1-5 carbon atoms; $R_2$ is selected from any one of alkylene having 1-5 carbon atoms, fluorine substituted alkylene having 1-5 carbon atoms or carbonyl;

in formula II, $R_3$, $R_4$, $R_5$, $R_6$, $R_7$ and $R_8$ are each independently selected from hydrogen, fluorine atom or a group containing 1-5 carbon atoms; and the percentage mass content of the compound B is 0.1-5% based on the total mass of the non-aqueous electrolyte for a lithium ion battery being 100%.

2. The non-aqueous electrolyte for lithium ion battery according to claim 1, wherein in the compound B represented by structural formula II, the group containing 1-5 carbon atoms is selected from hydrocarbyl, fluorinated hydrocarbyl, oxygen-containing hydrocarbyl, silicon-containing hydrocarbyl, or cyano-substituted hydrocarbyl.

3. The non-aqueous electrolyte for lithium ion battery according to claim 1, wherein each of $R_3$, $R_4$, $R_5$, $R_6$, $R_7$ and $R_8$ is independently selected from hydrogen atom, fluorine atom, methyl group, ethyl group, methoxy group, ethoxy group, trimethylsiloxy group, cyano group, or trifluoromethyl group.

4. The non-aqueous electrolyte for lithium ion battery according to claim 1, wherein the compound A represented by structural formula I is selected from

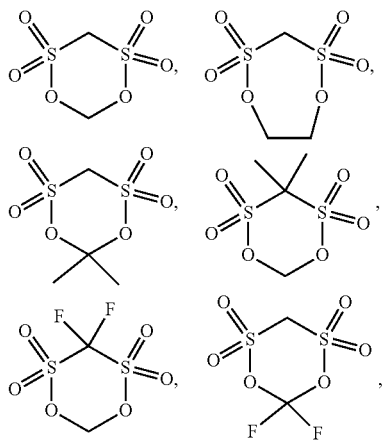

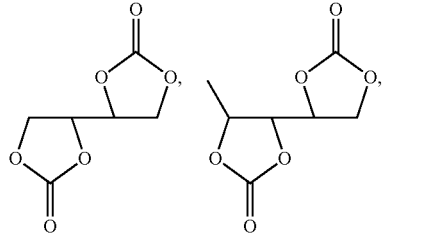

and the compound B represented by structural formula II is at least one selected from

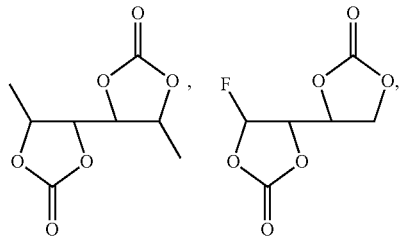

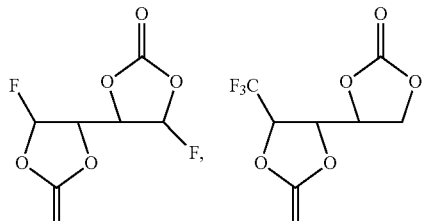

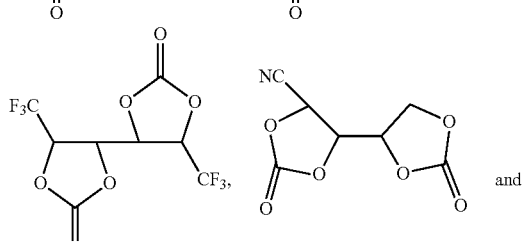

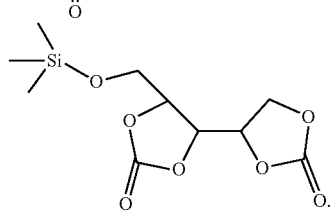

5. The non-aqueous electrolyte for lithium ion battery according to claim 1, wherein the percentage mass content of the compound A is 0.1% to 2.0% based on the total mass of the non-aqueous electrolyte for lithium ion battery being 100%.

6. The non-aqueous electrolyte for lithium ion battery according to claim 1, wherein the non-aqueous electrolyte further comprises at least one of unsaturated cyclic carbonate, fluorinated cyclic carbonate, and cyclic sultones.

7. The non-aqueous electrolyte for lithium ion battery according to claim 6, wherein the unsaturated cyclic carbonate further comprises at least one of vinylene carbonate, vinylethylene carbonate, and methylene vinyl carbonate;

the fluorinated cyclic carbonate comprises at least one of fluoroethylene carbonate, trifluoromethyl vinyl carbonate and difluoroethylene carbonate;

the cyclic sultones comprises at least one of 1,3-propane sultone, 1,4-butane sultone and propenyl-1,3-sultone.

8. A lithium ion battery, comprising a positive electrode, a negative electrode, a separator for separating the positive electrode and the negative electrode, and an electrolyte, wherein the electrolyte is the non-aqueous electrolyte for lithium ion battery according to claim 1.

9. The lithium ion battery according to claim 8, characterized in that the positive electrode comprises a positive electrode active material selected from at least one of $LiNi_xCo_yMn_zL_{(1-x-y-z)}O_2$, $LiCo_xL_{(1-x')}O_2$, $LiNi_{x''}L'_{y'}Mn_{(2-x''-y')}O_4$ and $Li_{z'}MPO_4$; wherein L is at least one of Al, Sr, Mg, Ti, Ca, Zr, Zn, Si or Fe; $0 \leq x \leq 1$, $0 \leq y \leq 1$, $0 \leq z \leq 1$, $0 < x+y+z \leq 1$, $0 < x' \leq 1$, $0.3 \leq x'' \leq 0.6$, $0.01 \leq y' \leq 0.2$; L' is at least one of Co, Al, Sr, Mg, Ti, Ca, Zr, Zn, Si, Fe; $0.5 \leq z' \leq 1$, M is at least one of Fe, Mn and Co.

* * * * *